(12) United States Patent
Garault et al.

(10) Patent No.: US 9,272,007 B2
(45) Date of Patent: Mar. 1, 2016

(54) **STRAIN OF *L. BULGARICUS* CAPABLE OF INHIBITING THE ADHESION OF *H. PYLORI* STRAINS TO EPITHELIAL CELLS**

(75) Inventors: Peggy Garault, Montlhery (FR); Gaelle Quere, Villebon sur Yvette (FR); Raphaelle Bourdet-Sicard, Palaiseau (FR); Francis Megraud, Bordeaux (FR)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 14/237,740

(22) PCT Filed: Aug. 9, 2011

(86) PCT No.: PCT/IB2011/053552
§ 371 (c)(1),
(2), (4) Date: Mar. 6, 2014

(87) PCT Pub. No.: WO2013/021239
PCT Pub. Date: Feb. 14, 2013

(65) Prior Publication Data
US 2014/0205571 A1   Jul. 24, 2014

(51) Int. Cl.
| | |
|---|---|
| *G01N 33/554* | (2006.01) |
| *G01N 33/569* | (2006.01) |
| *A61K 35/747* | (2015.01) |
| *A23L 1/30* | (2006.01) |
| *A23C 9/123* | (2006.01) |
| *C12N 1/20* | (2006.01) |
| *C12R 1/225* | (2006.01) |
| *C12N 15/74* | (2006.01) |

(52) U.S. Cl.
CPC ............. *A61K 35/747* (2013.01); *A23C 9/123* (2013.01); *A23C 9/1238* (2013.01); *A23L 1/3014* (2013.01); *C12N 1/20* (2013.01); *C12N 15/746* (2013.01); *C12R 1/225* (2013.01); *A23V 2200/00* (2013.01); *A23Y 2220/15* (2013.01)

(58) Field of Classification Search
None
See application file for complete search history.

(56) References Cited

PUBLICATIONS

Kabir et al. (Gut vol. 41, pp. 49-55, 1997).*
Boyanova et al., Anti-Helicobacter Pylori Activity of *Lactobacillus delbrueckii* Subsp. Bulgaricus Strains: Preliminary Report, Letters in Applied Microbiology, 48, pp. 579-584 (2009).
Simova et al., Characterization and Antimicrobial Spectrum of Bacteriocins Produced by Lactic Acid Bacteria Isolated from Traditional Bulgarian Dairy Products, Journal of Applied Microbiology, 106, pp. 692-701 (2009).
Fox JG, Inflammation, atrophy, and gastric cancer, J. Clin. Invest.,117:60-9, 2007.
Gury J et al., Random transposon mutagenesis of Lactobacillus plantarum by using the pGh9:IS S1 vector to clone genes involved in the regulation of phenolic acid metabolism Arch. Microbiol., 182:337-45, 2004.
Lee A et al., A Standardized Mouse Model of Helicobacter pylori Infection: Introducing the Sydney Strain Gastroenterology;112:1386-97, 1997.
Ménard A et al., PCR-Restriction Fragment Length Polymorphism Can Also Detect Point Mutation A2142C in the 23S rRNA Gene, Associated with Helicobacter pylori Resistance to Clarithromycin, Antimicrob. Agents Chemotherapy. 46:1156-7, 2002.
Oleastro M et al., Real-Time PCR Assay for Rapid and Accurate Detection of Point Mutations Conferring Resistance to Clarithromycin in Helicobacter pylori, J. Clin. Microbiol. 41:397-402, 2003.
Oleastro M, et al., Evaluation of the Clinical Significance of homB, a Novel Candidate Marker of Helicobacter pylori Strains Associated with Peptic Ulcer Disease, J. Infect. Dis.;198:1379-87, 2008.
Patnaik R et al., Genome shuffling of Lactobacillus for improved acid tolerance, Nat. Biotechnol.;20:707-12, 2002.
Perea Vélez M et al., Functional Analysis of D-Alanylation of Lipoteichoic Acid in the Probiotic Strain Lactobacillus rhamnosus GG, Appl Environ Microbiol.;73:3595-604, 2007.
Polk DB, Helicobacter pylori: gastric cancer and beyond, Nat. Rev. Cancer;10:403-14, 2010.
Wang Y et al., Genome-shuffling improved acid tolerance and I-lactic acid volumetric productivity in Lactobacillus rhamnosus, J. Biotechnol.;129:510-5, 2007.

* cited by examiner

*Primary Examiner* — Gary Nickol
*Assistant Examiner* — Khatol Shahnan Shah
(74) *Attorney, Agent, or Firm* — Morgan, Lewis & Bockius LLP

(57) ABSTRACT

The present invention relates to a new strain of *Lactobacillus delbrueckii* subsp. *bulgaricus*, suitable for use in the treatment or prevention of *Helicobacter pylori* infection.

11 Claims, 2 Drawing Sheets

STRAIN OF *L. BULGARICUS* CAPABLE OF INHIBITING THE ADHESION OF *H. PYLORI* STRAINS TO EPITHELIAL CELLS

The present invention relates to the field of probiotics. Particularly, the invention pertains to a new strain of *Lactobacillus delbrueckii* subsp. *bulgaricus*, useful for the treatment or the prevention of *Helicobacter pylori* infection.

According to a definition recently approved by the National Yogurt Association (NYA) or the International Life Science Institute (ILSI) in the USA, probiotics are living micro-organisms which upon ingestion in a sufficient amount exert health benefits beyond basic nutrition. Probiotic bacteria have been described among species belonging to the genera *Lactobacillus, Bifidobacterium, Streptococcus* and *Lactococcus*, commonly used in the dairy industry. Probiotics are thought to intervene at the level of the intestinal flora by impeding the development of pathogenic microorganisms and/or by acting more directly on the immune system.

*Helicobacter pylori* (*H. pylori*) is a Gram-negative spiral-shaped bacterium that colonizes the human gastric mucus layer of more than 50% of the world's population. While the majority of individuals infected with *H. pylori* is asymptomatic although their gastric epithelium show sign of inflammation, 15% to 20% of *H. pylori* infected individuals develop diseases. Indeed, *H. pylori* is the major causative agent of chronic active gastritis, peptic ulcer diseases, atrophy, metaplasia, dysplasia, gastric cancer and gastric mucosa associated lymphoid tissue (MALT) lymphoma (see for review Fox and Wang, 2007 and Polk and Peek, 2010).

During infection, *H. pylori* binds specifically to gastric epithelial cells lining the gastric epithelium through several adhesion molecules (adhesins) produced by the bacteria, such as BabA and SabA proteins. Adhesion to the gastric epithelial cells protects the bacteria from liquid flow, peristaltic movement and shedding of the mucous layer. *H. pylori* adhesion to the gastric mucosa induces signal transduction pathways within the gastric epithelial cells, leading to gastric epithelial cell damages and atrophy via oxidative stress, apoptosis and/or autophagy mechanisms. Accordingly, *H. pylori* adhesion to gastric epithelial cells is a key step in the establishment of an infection of the gastric mucosa.

The standard treatment in patients infected with *H. pylori* is two antibiotics associated to a proton pump inhibitor (PPI), so called triple therapy. However, *H. pylori* eradication rate following triple therapy is dropping down because of antibiotic resistance or poor compliance. Further, despite several clinical trials, there is no effective vaccine available on the market yet.

It appears from the foregoing that there is a need for alternatives or complements to triple therapy for the treatment or for the prevention of *H. pylori* infection.

It has been proposed, as an alternative, to use probiotic lactic acid bacteria (LAB) that produce lactic acid, bacteriocins and other antimicrobial substances. Boyanova et al. (2009) have found several *Lactobacillus delbrueckii* subsp. *bulgaricus* (*L. bulgaricus*) strains that inhibit the growth of *H. pylori* strains, including antibiotic-resistant strains, in vitro (using an agar-well diffusion method), in a strain-dependent manner. However, the studied *L. bulgaricus* strains are not clearly identified and are not publicly available. Simova et al. (2009) have screened several bacteriocin producing lactic acid bacteria. Then, they have determined the antimicrobial activity of said strains by analysing the antimicrobial activity of cell-free supernatant (CFS) of these strains by two in vitro methods: an agar-well diffusion method and the critical dilution assay of Barefoot and Klaenhammer. They have found that the CFS of the *L. bulgaricus* BB18 strain inhibits the growth of a wide spectrum of pathogenic micro-organisms (bacteria or yeast), including strains of *H. pylori*, due to its antimicrobial activity.

The inventors have isolated a new strain of *Lactobacillus delbrueckii* subsp. *bulgaricus* and have found, in vitro and in vivo, that this strain inhibits the adhesion of *H. pylori* strains to epithelial cells. This *L. bulgaricus* strain (named as DN_100_0602 or CNCM I-4428) can therefore be used for the treatment or the prevention of *H. pylori* infection, by targeting a major step in the establishment of this infection, namely by inhibiting the adhesion of *H. pylori* strains to epithelial cells.

Accordingly, a subject of the present invention is the strain *Lactobacillus delbrueckii* subsp. *bulgaricus* deposited, according to the Budapest Treaty, at CNCM (Collection Nationale de Cultures de Microorganismes, 25 rue du Docteur Roux, Paris) on Feb. 3, 2011, under the accession number CNCM I-4428.

This strain CNCM I-4428 has the following characteristics:
- Morphology: Gram-positive microorganism, immobile, rod-shaped, long bacilli with granulations,
- Metabolism: homofermentive, catalase (−),
- Fermentation of sugars (results obtained with an API 50 CH test in a MRS medium at 37° C. for 48 h): Glucose, Fructose, Mannose and Lactose.

Further, this strain is capable of inhibiting the adhesion of *H. pylori* strains to epithelial cells in vitro and in vivo.

As used herein, the term "inhibiting the adhesion of *H. pylori* strains to epithelial cells" refers to a significant inhibition (i.e., total or partial inhibition) of the adhesion of *H. pylori* strains to epithelial cells. The inhibition of the adhesion of *H. pylori* strains to epithelial cells can be measured in vitro as shown in Example 1 below.

The present invention also encompasses mutant strains or genetically transformed strains derived from the parent strain CNCM I-4428, provided that they are capable of inhibiting the adhesion of *H. pylori* strains to epithelial cells. These mutant or genetically transformed strains can be strains wherein one or more endogenous gene(s) of the parent strain has (have) been mutated, for instance to modify some of its metabolic properties (e.g., its ability to ferment sugars, its resistance to acidity, its survival to transport in the gastrointestinal tract, its post-acidification properties or its metabolite production). They can also be strains resulting from the genetic transformation of the parent strain CNCM I-4428 by one or more gene(s) of interest, for instance in order to confer to said genetically transformed strains additional physiological features, or to allow it to express proteins of therapeutic or vaccinal interest that one wishes to administer through said strains. These strains can be obtained from the CNCM I-4428 strain by means of the conventional techniques for random or site-directed mutagenesis and genetic transformation of Lactobacilli, such as those described by Gury et al. (2004) or by Perea Vélez et al., 2007, or by means of the technique known as "genome shuffling" (Patnaik et al., 2002 and Wang et al., 2007).

A subject of the present invention is also a method for obtaining a strain of *Lactobacillus delbrueckii* subsp. *bulgaricus* capable of inhibiting the adhesion of *H. pylori* strains to epithelial cells, comprising a step of mutagenesis or genetic transformation of the strain CNCM I-4428.

A subject of the present invention is also cell fractions which can be obtained from a *L. bulgaricus* strain as defined above, preferably the strain CNCM I-4428, provided that they are capable of inhibiting the adhesion of *H. pylori* strains to epithelial cells. They are in particular DNA preparations or bacterial wall preparations obtained from cultures of said strain. They may also be culture supernatants or fractions of these supernatants. By way of example, cell-free supernatant (CFS) of the strain CNCM I-4428 can be obtained using the method for obtaining a CFS from another *L. bulgaricus* strain, disclosed in Simova et al., 2009.

A subject of the present invention is also a method for obtaining a cell fraction which is capable of inhibiting the adhesion of *H. pylori* strains to epithelial cells, comprising the steps of:
 a) culturing a *L. bulgaricus* strain as defined above, preferably the strain CNCM I-4428, and
 b) obtaining the cell fraction from the culture in step a).

A subject of the present invention is also a composition comprising a *L. bulgaricus* strain according to the present invention, preferably the strain CNCM I-4428, or a cell fraction obtained from said strain according to the present invention.

In the composition of the invention, said strain can be used in the form of whole bacteria which may be living or dead. Alternatively, said strain can be used in the form of a bacterial lysate or in the form of bacterial fractions; the bacterial fractions suitable for this use can be chosen, for example, by testing their properties on the adhesion of *H. pylori* strains to epithelial cells. Preferably the bacterial cells are present as living, viable cells.

The compositions of the invention can be in any form suitable for administration, in particular oral administration. This includes for instance solids, semi-solids, liquids, and powders. Liquid composition are generally preferred for easier administration, for instance as drinks.

The composition can comprise at least $10^5$ cfu, preferably at least $10^6$ cfu, per g dry weight, of at least one bacterial strain as mentioned above.

The composition can further comprise other strains of bacteria than the strains according to the present invention, in particular probiotic strain(s), such as *Lactobacillus*, *Bifidobacterium*, *Streptococcus* or *Lactococcus* strain(s).

When the bacteria are in the form of living bacteria, the composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

The composition can be a nutritional composition, including food products, food supplements and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

The nutritional composition according to the invention also includes a baby food, an infant milk formula or an infant follow-on formula. Preferably the present composition is a nutraceutical or a pharmaceutical product, a nutritional supplement or medical food.

The composition can be a dairy product, preferably a fermented dairy product. The fermented product can be present in the form of a liquid or in the form of a dry powder obtained by drying the fermented liquid. Examples of dairy products include fermented milk and/or fermented whey in set, stirred or drinkable form, cheese and yoghurt.

The fermented product can also be a fermented vegetable, such as fermented soy, cereals and/or fruits in set, stirred or drinkable forms.

In a preferred embodiment, the fermented product is a fresh product. A fresh product, which has not undergone severe heat treatment steps, has the advantage that the bacterial strains present are in the living form.

A subject of the present invention is also a *L. bulgaricus* strain as defined above, preferably the strain CNCM I-4428, or a composition as defined above for use as a medicament.

A subject of the present invention is also a *L. bulgaricus* strain as defined above, preferably the strain CNCM I-4428, or a composition as defined above for use as a medicament for treating or preventing *Helicobacter pylori* infection.

A subject of the present invention is also the use of a *L. bulgaricus* strain as defined above, preferably the strain CNCM I-4428, or a composition as defined above as a medicament, preferably a medicament for treating or preventing *H. pylori* infection.

A subject of the present invention is also the use of a *L. bulgaricus* strain as defined above, preferably the strain CNCM I-4428, or a composition as defined above for the manufacture of a medicament, preferably a medicament for treating or preventing *H. pylori* infection.

A subject of the present invention is also a method for treating or preventing *H. pylori* infection in a subject in need thereof, said method comprising administering to said subject a therapeutically effective amount of a *L. bulgaricus* strain as defined above, preferably the strain CNCM I-4428, or a composition as defined above.

Determination of a therapeutically effective amount is well known from the person skilled in the art, especially in view of the detailed disclosure provided herein.

A subject of the present invention is also a method for the manufacture of a medicament, preferably a medicament for treating or preventing *H. pylori* infection, said method comprising incorporating a *L. bulgaricus* strain as defined above, preferably the strain CNCM I-4428, or a composition as defined above, into at least one pharmaceutically acceptable diluent, carrier or excipient.

As used herein, the treatment or prevention encompasses inter alia: preventive infection, stabilizing the load of *H. pylori* and/or decreasing the load of *H. pylori*. The treatment or prevention also encompasses addressing at least one of the symptoms associated with *H. pylori* mentioned below.

Methods for diagnosing *H. pylori* infection are known in the art. By way of example, diagnosis of *H. pylori* infection can be made by a blood antibody test, a stool antigen test or the carbon urea breath test. It can also be made by biopsy under endoscopy followed by a urease test, a histological examination or a microbial culture.

The symptoms or diseases associated with *H. pylori* infection are stomach ache, heartburn, acid reflux, abdominal pain, regurgitation, vomiting, belching, flatulence, nausea, gastritis such as chronic active gastritis, peptic ulcer diseases, atrophy, metaplasia, dysplasia, gastric cancer and gastric mucosa associated lymphoid tissue (MALT) lymphoma.

The present invention will be understood more clearly from the further description which follows, which refers to examples illustrating the anti-infective properties of the CNCM I-4428 strain as well as to the appended figures.

EXAMPLE 1

Figure 1:
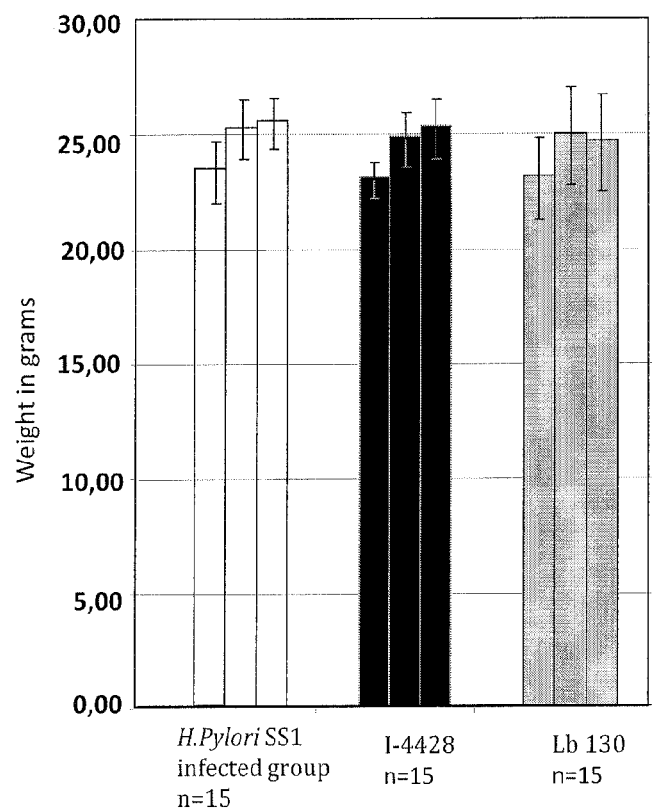
FIG. 1 shows weight evolution (in grams) of mice infected by *H. pylori* SS1 receiving a controlled product, or infected by *H. pylori* SS1 and treated with *L. bulgaricus* CNCM I-4428, or infected by *H. pylori* SS1 and treated with *L. bulgaricus* CNCM I-1632 (Lb 130), measured just before the treatment (first bar), 3 weeks after the treatment (second bar) and just before sacrifice (third bar).

Selection of *L. bulgaricus* Strains for Their Effect on Adhesion of *Helicobacter pylori* to Gastric Epithelial Cells The method described by Oleastro et al. (2008) was used with modifications to assess the effect of two *Lactobacillus delbrueckii* subsp. *bulgaricus* strains (CNCM I-4428 and CNCM I-1632 deposited at CNCM on Oct. 25, 1995) on the adhesive properties of *H. pylori* to epithelial cells.

1.1 Material & Methods

Two *H. pylori* strains were tested: the strain J99 (BabA2; ATCC number: 700824) and the strain 09.193 (BabA1, isolated in Japan by Yoshio Yamaoka, from Oita University). These strains were tested with a MOI (multiplicity of infection) of 50. *H. pylori* cells were transferred in PBS buffer after a culture of 24 h in pylori agar (Biomérieux, France). The concentration of bacterial suspensions of the two strains of *H. pylori* respectively was normalised at $2.10^8$ cfu/mL (corresponding to $OD_{600\,nm}=1$).

Two *Lactobacillus delbrueckii* subsp. *bulgaricus* suspensions were tested with a MOI of 50 (corresponding to 254, of normalized suspension of the *L. bulgaricus* by well).

100 000 epithelial AGS cells (ATCC number: CRL-1739) were inoculated the day before the experiment of infection in 500 µL of DMEM medium F12 complemented with foetal bovine serum at 10%.

Coloration of *H. pylori* Suspensions 1 mL of *H. pylori* suspension was centrifuged 10 minutes at 10 000 g. The pellet was resuspended in 1 mL of Diluent A (from the PKH2 Green Fluorescent Cell Linker Kit, Sigma Aldrich, Saint-Louis) and 2.50, of $PKH_2$ (Sigma Aldrich, Saint-Louis) were added. The suspension was incubated 2 minutes and 30 seconds at room temperature. The coloration was stopped by addition of 2 mL of foetal bovine serum. Then 4 mL of DMEM/F12 medium were added before the centrifugation of the suspension for 10 minutes at 10 000 g. The pellet was resuspended in 4 mL of culture medium and centrifuged 10 minutes at 10 000 g. This washing step was repeated twice to remove excess fluorochrome.

Measurement of Adhesion

Epithelial AGS cells were dissociated with trypsin following standard conditions after three washings with PBS to discard non adherent bacteria. Fluorescent emission was analysed by flow cytometry. Fluorescence was measured using the FACSCalibur flow cytometer (Becton Dickinson). Each condition was carried out in triplicates.

Infection with *H. pylori* was Carried Out in Two Conditions in pre-infection (pre) condition: the *L. bulgaricus* suspension to be tested was added to the epithelial AGS cells 1 h 30 before the infection with *H. pylori*. Cells were analysed by flow cytometry 1 h 30 after the infection (total incubation time 3 h);

in co-infection (co) condition: the *L. bulgaricus* suspension to be tested and a *H. pylori* strain were added to the epithelial AGS cells at the same time and the cells were analysed by flow cytometry after an incubation time of 1 h 30.

Control

The control value of fluorescence intensity is obtained with the epithelial AGS cells incubated with *H. pylori* strains for 1 h 30.

Percent adhesion values are given relative to the adhesion of *H. pylori* to epithelial AGS cells without exposure to *L. bulgaricus*, which were set at 100%.

Results were analyzed from the mean value obtained from triplicates and they were scored when they were significantly different according to Student's test ($P<0.05$).

1.2 Results

The results are shown in Table 1 hereafter.

TABLE 1 results obtained with 2 strains of *L. bulgaricus* for their effect on adhesion of *H. pylori* to epithelial AGS cells.

| | *H. pylori* strains | | | |
|---|---|---|---|---|
| | J99 | | 09.193 | |
| | condition | | | |
| *L. bulgaricus* strains | pre | co | pre | co |
| *L. bulgaricus* CNCM I-4428 Mean scores obtained | 1.5 | 0.9 | 2.1 | 1.4 |
| *L. bulgaricus* CNCM I-1632 Mean scores obtained | 0 | 0 | 0 | 0 |

Definition of scores: −3: significant increase in adhesion, 0: non significant effect on adhesion, 1: significant inhibition of adhesion from 1 to 10%, 2: significant inhibition of adhesion from 11 to 20%, 3: significant inhibition of adhesion from 21 to 30%, 4: significant inhibition of adhesion superior to 30%.

The results show that a bacterial suspension of the strain CNCM I-4428 inhibits the adhesion of two *H. pylori* strains (J99 and 09.193) to epithelial AGS cells in two different conditions (pre- and co-incubation), but that a bacterial suspension of the strain CNCM I-1632 does not have this property.

EXAMPLE 2

Effect of the Strain CNCM I-4428 on the Load of *H. pylori* in a Mice Model 2.1 Material & Methods

*Helicobacter pylori*

*H. pylori* strain SS1 having a very good colonization ability of mouse gastric mucosa (Lee et al., 1997) was used. Identity of the strain was checked by sequencing the genes glm and hspA and vacA.

*Lactobacillus delbrueckii* subsp. *bulgaricus*

Milk products fermented by 2 different strains of *L. bulgaricus* (CNCM I-4428 or CNCM I-1632) were prepared as follows: First culture in MRSn was prepared from frozen strain and incubated at 37° C. for 17 h. A second culture was prepared in skimmed milk enriched with yeast extract (2 g/L) by inoculation at 1% from the first culture and incubated at 37° C. for 17 h. A third culture was prepared in milk enriched with yeast extract (2 g/L) by inoculation at 1% from the second culture and incubation at 37° C. until pH 4.7 was reached. The product was finally prepared by inoculation of milk enriched with yeast extract (2 g/L) at 1% with the third culture until pH 4.7 was reached. Products were stored at −80° C. Bacterial count was carried out in MRSn after 48 h incubation. Bacterial count was $6 \cdot 10^8$ and $1.3 \cdot 10^9$ cfu/mL respectively for strains CNCM I-4428 and CNCM I-1632.

Mice

55 BALB/cBy/J female mice of 5 weeks old (Charles River, France) and tested as SPF (<<specific pathogen free>>) were split into groups: 3 groups of 15 mice were infected and 1 group of 10 mice was used as non infected control. Mice were fed with food poor in vitamins to enhance the lesion development induced by *H. pylori*.

Infection (8 Weeks)

6 weeks old mice received a hydric diet for 1 day and then were force-fed the following morning with 250 μL of an enriched suspension of the strain *H. pylori* SS1 (1 to 2 Petri dishes of *H. pylori* for 5 mice). The mice were put in a cage with a normal diet. Then, the mice received a hydric diet again in the evening. This protocol was repeated for 3 days.

Treatment (6 Weeks)

Eight weeks after their infection, mice were treated for 6 weeks with milk products containing a *L. bulgaricus* strain. 120 g of milk product were given per cage per day in feeding-bottles instead of water. The feeding-bottles were changed every day. To assess the quantity of products ingested per animal, the feeding-bottles were weighed. Further, mice were weighted just before the treatment, 3 weeks after the treatment and just before sacrifice (results are shown in FIG. 1).

Mice control groups received milk enriched with yeast extract (2 g/L) (i.e., without any *L. bulgaricus* strain).

Sacrifices

Mice were sacrificed by cervical dislocation. Laparotomy was performed. Stomachs were isolated and gastric mucosa was washed in physiological serum.

Stomach was cut through the middle from the esophagus to the duodenum. For the right half stomach, cardia was eliminated, and then this half stomach was put in physiological serum to be used for the molecular study. The left half stomach was used for histology.

Histology

The left half stomach was fixed 1 night in 3.7% formol and washed with 70% ethanol and then paraffin-embedded and sectioned at 3 μM thickness.

Immunohistochemistry was carried out with an antibody anti-*H. pylori* antigens: primary antibody: anti-*H. pylori* (Dako, Ref. B0471); secondary antibody and DAB: Dako EnVision+ System-HRP (DAB) (Dako, Ref. K4011).

Molecular Study (q RT-PCR)

Right stomachs were homogenized (disrupted) in 0.2 ml physiological serum with a Potter-Elvehjem (the tube was weighted with and without the stomach tissue to know the weight of the tissue).

Total DNA was extracted from the crushed stomach with Arrow Stool DNA kit (NorDiag, Norvège) following supplier recommendations. For each crushed stomach total DNA was resuspended in 180 TRIS buffer (10 mM).

Presence of DNA of *H. pylori* was quantified in DNA extracts by Real-Time PCR. Amplification was done with primers targeting 23S rRNA, present in two copies in *H. pylori* following the method described by Oleastro et al. (2003). For 20 μl of mix ($MgCl_2$ 25 mM, primers HPY-A et HPY-S 20 μM described by Ménard et al., 2002, sensor probe that is 5' labeled with LC-Red 640 and 3' phosphorylated and anchor probe that is 3' labeled with fluorescein (both probes described by Oleastro et al. 2003) 20 μM, buffer containing the enzyme (10×, kit FastStart DNA Master Hybridization Probes, Roche Diagnostics), 5 μl DNA at 200 ng/μl was added to be amplified in Light Cycler ROCHE, using the following program:

| Denaturation: | 95° C. | 10 min | |
| Amplification: | 50 cycles | | 20° C./sec |
| | 95° C. | 0 sec | |
| | 60° C. | 20 s | |
| | 72° C. | 12 sec | |
| Fusion: | 95° C. | 0 sec | |
| | 38° C. | 50 sec | 20° C./sec |

2.2 Results

Figure 2:
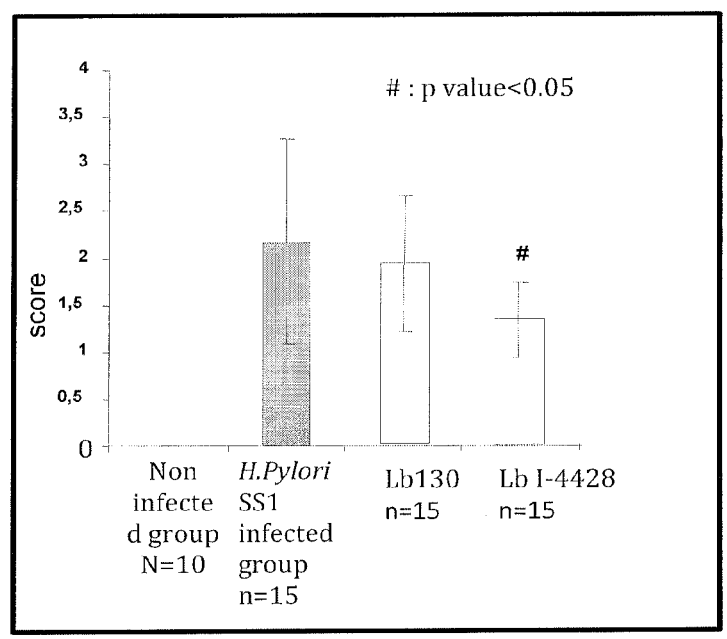
FIG. 2 shows the score of infection obtained by immunohistochemistry using anti-*H. pylori* antibodies in mice (i) non-infected by *H. pylori*, (ii) infected by *H. pylori* SS1 receiving a controlled product (non-fermented milk), (iii) infected by *H. pylori* SS1 and treated with *L. bulgaricus* CNCM I-1632 (Lb 130) and (iv) infected by *H. pylori* SS1 and treated with *L. bulgaricus* CNCM I-4428. Definition of scores: 0: no infected gland, 1: rare infected glands, 2: 25% infected glands, 3: from 25 to 50% infected glands, 4: >50% infected glands.

The scores of infection obtained by immunohistochemistry for the *L. bulgaricus* strains CNCM I-4428 and CNCM I-1632 (Lb 130) are shown in FIG. 2. These results show that administration of milk product fermented with the strain CNCM I-4428 to mice infected by *H. pylori* significantly decreases the score of infection but that the treatment with the milk product fermented with the strain CNCM I-1632 does not decrease the load of *H. pylori*.

Figure 3:
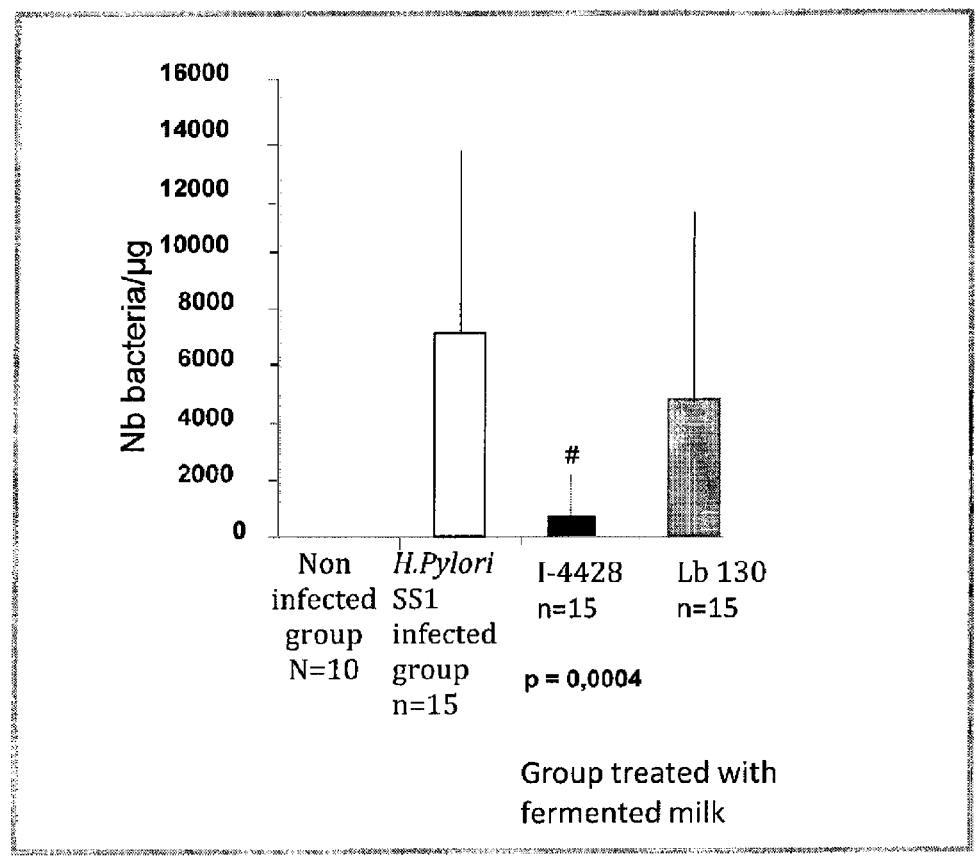
FIG. 3 shows the quantification of *H. pylori* SS1 DNA obtained by Real-Time PCR in mice (i) non-infected by *H. pylori*, (ii) infected by *H. pylori* SS1 but receiving a controlled product (non-fermented milk), (iii) infected by *H. pylori* SS1 and treated with *L. bulgaricus* CNCM I-4428 and (iv) infected by *H. pylori* SS1 and treated with *L. bulgaricus* CNCM I-1632 (Lb 130).

The results obtained by Real-Time PCR for the *L. bulgaricus* strains CNCM I-4428 and CNCM I-1632 (Lb 130) are shown in FIG. 3. These results show that, in mice, the treatment with the milk product fermented with the strain CNCM I-4428 significantly decreases the load of *H. pylori* but that the treatment with the milk fermented with the strain CNCM I-1632 does not decrease the load of *H. pylori*.

REFERENCES

Boyanova L et al., Lett Appl Microbiol. 2009; 48:579-84.
Fox J G and Wang T C., J Clin Invest. 2007; 117:60-9.
Gury J et al., Arch Microbiol. 2004; 182:337-45.
Lee A et al., Gastroenterology. 1997; 112:1386-97.
Ménard A et al., Antimicrob Agents Chemother. 2002; 46:1156-7.
Oleastro M et al., J Clin Microbiol. 2003; 41:397-402.
Oleastro M, et al., J Infect Dis. 2008; 198:1379-87.
Patnaik R et al., Nat Biotechnol. 2002; 20:707-12.
Perea Vélez M et al., Appl Environ Microbiol. 2007; 73:3595-604.
Polk D B and Peek R M Jr., Nat Rev Cancer. 2010; 10:403-14.
Simova E D et al., J Appl Microbiol. 2009; 106:692-701.
Wang Y et al., J Biotechnol. 2007; 129:510-5.

The invention claimed is:

1. A genetically transformed *Lactobacillus delbrueckii* subsp. *bulparicus* (*L. bulparicus*) strain derived from the parent strain *Lactobacillus bulparicus* deposited with the Collection Nationale De Cultures De Microorganismes (CNCM) under accession number I-4428, wherein one or more endogenous gene(s) of the parent strain are mutated and/or one or more gene(s) of interest are transformed into the parent strain, wherein said genetically transformed *L. bulparicus* strain is capable of inhibiting adhesion of *Helicobacter pylori* strains to epithelial cells.

2. A cell fraction obtained by a method comprising:
(a) culturing a *L. bulparicus* strain, wherein the *L. bulparicus* strain is
   (i) a *L. bulparicus* strain deposited with the CNCM under Accession number I-4428, or
   (ii) a genetically transformed *L. bulparicus* strain of claim 1, and
(b) isolating the cell fraction from the culture in step a), wherein said cell fraction inhibits the adhesion of *H. pylori* strains to epithelial cells.

3. A fermented dairy product composition comprising a *Lactobacillus delbrueckii* subsp. *bulgaricus* strain deposited with the CNCM under Accession number I-4428 or a genetically transformed *L. bulgaricus* strain of claim 1.

4. The composition according to claim 3, comprising at least $10^5$ cfu per gram dry weight of the *L. bulgaricus* strain.

5. The composition according to claim 3, wherein the composition is a nutritional composition.

6. The composition according to claim 5, wherein the composition is a yogurt product.

7. A composition comprising the cell fraction according to claim 2.

8. The composition according to claim 7, wherein the composition is a nutritional composition.

9. The composition according to claim 8, wherein the composition is a dairy product.

10. A pharmaceutical composition comprising the cell fraction according to claim 2.

11. The composition according to claim 4, comprising at least $10^6$ cfu per gram dry weight of the *L. bulgaricus* strain.

* * * * *